(12) United States Patent
Hofmann et al.

(10) Patent No.: US 7,112,680 B2
(45) Date of Patent: Sep. 26, 2006

(54) HETEROCYCLIC HYDRAZONES FOR USE AS ANTI-CANCER AGENTS

(75) Inventors: Johann Hofmann, Innsbruck (AT); Gottfried Heinisch, Innsbruck (AT); Johnny Easmon, Innsbruck (AT); Gerhard Pürstinger, Innsbruck (AT); Heinz-Herbert Fiebig, Freiburg (DE)

(73) Assignee: Austria Wirtschaftsservice Gesellschaft MIT Beschrankter Haftung, Vienna (AT)

( * ) Notice: Subject to any disclaimer, the term of this patent is extended or adjusted under 35 U.S.C. 154(b) by 240 days.

(21) Appl. No.: 10/297,306

(22) PCT Filed: Jun. 5, 2001

(86) PCT No.: PCT/AT01/00187

§ 371 (c)(1),
(2), (4) Date: Jan. 7, 2003

(87) PCT Pub. No.: WO01/94340

PCT Pub. Date: Dec. 13, 2001

(65) Prior Publication Data

US 2003/0166658 A1    Sep. 4, 2003

(30) Foreign Application Priority Data

Jun. 5, 2000    (AT)    .................... 977/2000

(51) Int. Cl.
A61K 31/44    (2006.01)
A01N 43/42    (2006.01)
(52) U.S. Cl. .............. 548/304.4; 548/302.7; 548/302.2
(58) Field of Classification Search ............ 548/302.7, 548/302.4, 304.4
See application file for complete search history.

(56) References Cited

U.S. PATENT DOCUMENTS 3,525,622 A * 8/1970 Willems et al. ............. 430/591
3,600,165 A * 8/1971 Willems et al. ............. 430/90

FOREIGN PATENT DOCUMENTS

WO    WO 97/15308 A1    5/1997

OTHER PUBLICATIONS

Hall et al., "Investigations on the mechanism of action of the novel antitumor agents 2-benzothiazolyl . . . ", Archiv der Pharmazie (Weinheim, Germany) (1999), 332(4), 115-123.*

Easmon, J. et al, "Thiazolyl and benzothiazolyl hydrazones derived from.alpha.—(N)—acetylpyridines and diazines: synthesis, antiproliferative activity and CoMFA studies", Eur. J. Med. Chem, pp. 397-408, (1997).

Hall, Iris H. et al.,. "Investigation on the mechanism of action of the novel antitumor agents 2-benzothiazolyl, 2-benzoxazolyl, and 2-benzimidazolyl: hydrazones derived from 2-acetylpyridine", Arch. Pharm. Pharm. Med. Chem, pp. 115-123, (1999).

(Continued)

Primary Examiner—James O. Wilson
Assistant Examiner—Paul V. Ward
(74) Attorney, Agent, or Firm—Birch, Stewart, Kolasch & Birch, LLP

(57) ABSTRACT

The invention relates to novel 2-benzimidazolyl-, 2-benzoxazolyl- and 2-benzothiazolyl hydrazones that are derived from 2-formylpyridine, 2-acylpyridines, acetyldiazines and acetyl(iso)quinolines. The invention also relates to a novel method for producing 2-benzimidazolyl-, 2-benzoxazolyl- and 2-benzothiazolyl hydrazones and to their use as useful anti-cancer therapeutic agents. The novel compounds are also active against multidrug-resistant cancer cells.

8 Claims, 1 Drawing Sheet

OTHER PUBLICATIONS

Pellerano, C. et al., "Tridentate N-N-N chelating systems as potential antitumoral agents", IL FARMACO, pp. 645-654, (1985).

Singh, Raj Bhushan et al., "Spectrophotometric and analog derivative spectrophotometric determination of cobalt with 2,2'-dipyridyl-2-benzothiazolylhydrazone", Analyst, Jan., vol. 109, pp. 43-46, (1984).

Otomo, Makoto et al., "Benzothiazole-2-aldehyde-2-quinolylhydrazone as a reagent for the extractive spectrophotometric determination of copper (II)", Microchem. J., vol. 23, pp. 297-304, (1978).

Kwon, Sundo et al., "Geometrical isomers of hydrazones from 2-formyl-, 2-acetyl-, and 2-benzylpyridine, and 2-hydrazinobenzothiazole", Nippon Kagaku Kaishi, vol. 7, pp. 1314-1319, (1973).

* cited by examiner

HETEROCYCLIC HYDRAZONES FOR USE AS ANTI-CANCER AGENTS

This application is the national phase under 35 U.S.C. § 371 of PCT International Application No. PCT/AT01/00187 which has an International filing date of Jun. 5, 2001, which designated the United States of America.

The present invention relates to novel 2-benzimidazolyl, 2-benzoxazolyl, and 2-benzothiazolyl hydrazones derived from 2-formylpyridine, 2-acylpyridines, acetyl diazines and acetyl(iso)quinolines, a novel method of producing 2-benzimidazolyl, 2-benzoxazolyl, and 2-benzothiazolyl hydrazones as well as their utilization as useful therapeutic anti-cancer agents. Furthermore, these compounds are also active against cancer cells exhibiting a multidrug resistance.

Despite new findings in tumor biology, surgical intervention, irradiation and antitumor substances continue to play major roles in tumor therapy. Disadvantages of the antitumor substances available to date are serious side effects, low response rates in solid tumors, and the development of resistance. In particular in colon carcinomas, one of the most frequently occurring tumors in the Western hemisphere, chemotherapy shows only little efficacy. Therefore, more effective antitumor substances would be desirable.

The enzyme ribonucleotide reductase (RR) represents an important target molecule in cancer chemotherapy. With the intention of developing a new class of RR inhibitors, the N—N—S pharmacophore of α-(N)-heteroaromatic thiosemicarbazones, for example compounds (1) and (2), were used as a starting point.

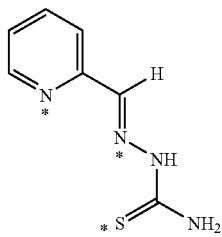

(1)

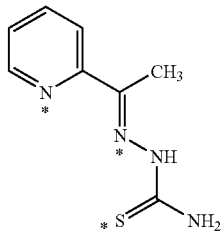

(2)

Furthermore, 2-benzothiazolyl and 2-thiazolyl hydrazones derived from 2-formyl pyridine, e.g. compounds (3) and (4)

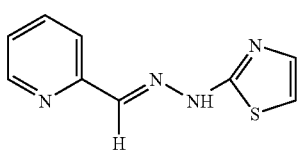

(3)

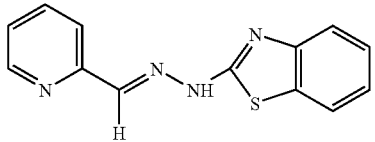

(4)

and 2-acetyl pyridines, respectively, e.g. compounds 5 and 6,

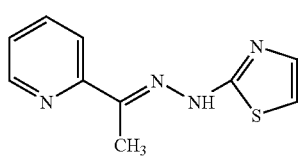

(5)

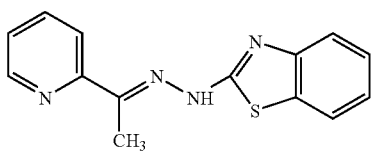

(6)

have already been synthesised.

These compounds have already been tested in vitro against a panel of human tumor cell lines, with the known compounds (1) and (2) serving as controls. The hydrazones (3) and (5) turned out to be 5 to 10 times more active than the known thiosemicarbazones (1) and (2) (see Easmon et al., *Eur. J. Med. Chem.*, 32, 397, 1997). Furthermore, it has also been possible to show that the compounds (3) to (6) do not exhibit any cross-resistance against a leukaemia cell line which overexpresses the M2 protein subunit. However, in this connection it has also been found that the compounds (3) to (6) do not inhibit RR and that the N—N—S pharmacophore is not relevant for this class of active substances. This assumption has also been supported by the fact that these compounds bind metal ions in the N—N—N form, as revealed by the x-ray structural analysis of the nickel complex of compound (6).

In furtherance of the efforts to develop new anti-tumor agents, hydrazones in which the 2-benzothiazolyl ring system has been substituted by a 2-benzimidazolyl or a 2-benzoxazolyl ring system have now been synthesized according to the invention. This has led to a novel class of hydrazones which exhibits potent cytotoxic and anti-tumor activities and are also useful against multidrug resistant tumors.

The antiproliferative activity of the novel substances has been tested in various human tumor cell lines. Effective compounds have then been tested in the clonogenic assay (inhibition of colony formation of human tumor grafts in soft agar).

Some of the compounds have been tested in mice transplanted with human CXF 280 colon tumor cells (human tumor grafts) directly into the flanks. In all experiments, the substances have shown antitumor activity, in particular against colon tumors.

Seeking intensively for compounds having anti-tumor activity, it has now surprisingly been found that novel hydrazones, derived from (benzoannelated) α-(N)-formyl and acyl (di)azines and 2-hydrazinobenzimidazoles, 2-hydrazinobenzoxazoles or 2-hydrazinobenzothiazoles exhibit a remarkable anti-tumor activity both in vitro and also in vivo.

The present invention now relates to new compounds of the general formula

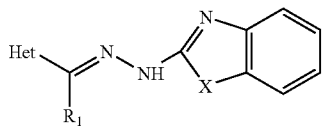

wherein Het=

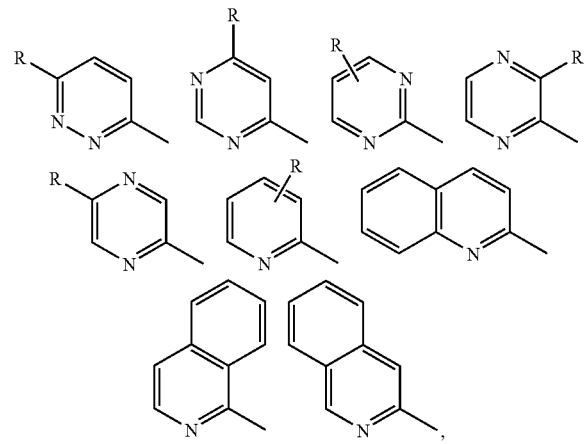

and wherein R=H, CH$_3$, OCH$_3$, OH, Cl, Br, F, CF$_3$, NO$_2$, NH$_2$, NHCOCH$_3$, N(CH$_3$)$_2$, phenyl, CN, C=NH(NH$_2$), C=S(NH$_2$), C=NH(NHOH), COOH or COOR$_4$, wherein R$_4$=an aliphatic residue or a phenyl group, or CONR$_5$R$_6$, wherein R$_5$ and R$_6$ represent H, an aliphatic substituent or a phenyl group, R$_1$=H, methyl, ethyl, propyl, iso-propyl, butyl, tert.-butyl, cyclopropyl, cyclohexyl, phenyl, benzyl or 2-pyridyl, and X=O, S, NH or N—R$_2$, wherein R$_2$=methyl, ethyl, propyl, sec.-propyl, butyl, tert.-butyl, allyl, cyclopropyl, phenyl, benzyl, CH$_2$—CH$_2$—O—CH$_3$ or CH$_2$—CH$_2$—N(CH$_3$)$_2$, with the proviso that if

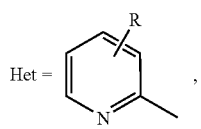

wherein R=H,
in case X=S: R$_1$ is not H, methyl, phenyl or 2-pyridyl,
in case X=O: R$_1$ is not methyl,
in case X=N: R$_1$ is not H,
in case X=NH: R$_1$ is not methyl,
in case X=N—R$_2$ with R$_2$=CH$_3$: R$_1$ is not methyl;

with the further proviso that if

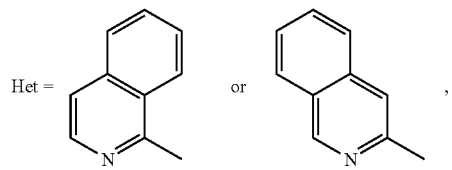

in case X=S: then R$_1$ is not methyl;
with the further proviso that if

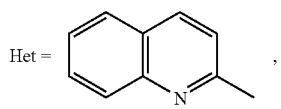

in case X=S: R$_1$ is not H or methyl;
with the further proviso that if

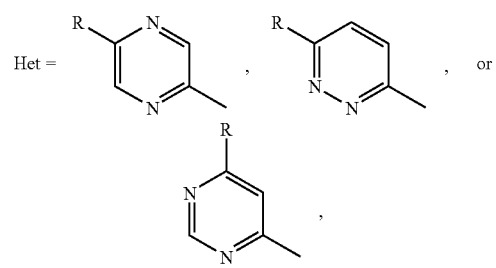

in case X=S and R$_1$ methyl: R is not H or methyl;
with the further proviso that if

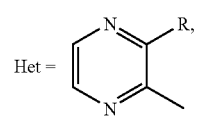

in case X=S and R$_1$=methyl: R is not methyl;
with the further proviso that if

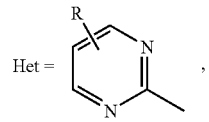

in case X=S and R$_1$=methyl: R is not H;
as well as with the proviso that if

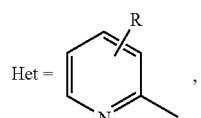

in case X=S and R$_1$=H: R in position 6 is not methyl;

as well as the pharmaceutically acceptable salts thereof.

The present invention also relates to a method of producing a compound of the general formula

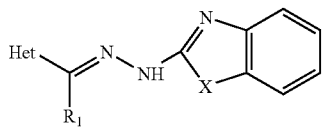

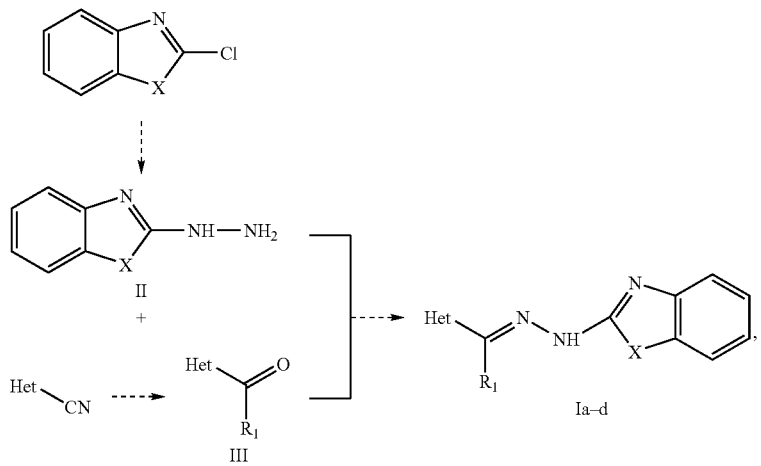

wherein Het=

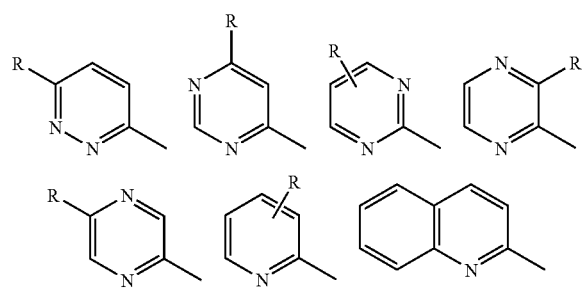

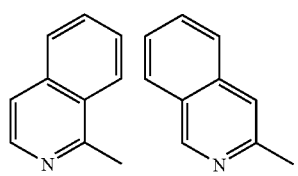

and wherein R=H, $CH_3$, $OCH_3$, OH, Cl, Br, F, $CF_3$, $NO_2$, $NH_2$, $NHCOCH_3$, $N(CH_3)_2$, phenyl, CN, $C=NH(NH_2)$, $C=S(NH_2)$, $C=NH(NHOH)$, COOH or $COOR_4$, wherein $R_4$=an aliphatic residue or a phenyl group, or $CONR_5R_6$, wherein $R_5$ and $R_6$ are H, an aliphatic substituent or a phenyl group, $R_1$=H, methyl, ethyl, propyl, iso-propyl, butyl, tert.-butyl, cyclopropyl, cyclohexyl, phenyl, benzyl or 2-pyridyl, and X=O, S, NH or N—$R_2$, wherein $R_2$=methyl, ethyl, propyl, sec.-propyl, butyl, tert.-butyl, allyl, cyclopropyl, phenyl, benzyl, $CH_2$—$CH_2$—O—$CH_3$ or $CH_2$—$CH_2$—$N(CH_3)_2$, with the proviso that if X=S and Het=pyridinyl, then $R_1$ is not H or methyl, by reaction of suitable ketones with suitably substituted hydrazines. In particular, the above-mentioned compounds as well as suitable intermediate compounds can be produced by the following method:

wherein Het, R, $R_1$, $R_2$, $R_3$, $R_4$, $R_5$, $R_6$ and X are as defined above, with the proviso that if X=S and Het=pyridinyl, then R is not H or methyl.

The hydrazones of type Ia-d are synthesised by heating a ketone (III) and a hydrazine (II) in methanol or ethanol with the addition of a catalytic amount of a suitable acid, such as, e.g., acetic acid, hydrochloric acid or sulfuric acid. Alternatively, the synthesis can be performed also at room temperature, yet then it will take several days until the reaction is complete. The hydrazines of type II are prepared by heating to reflux the respective 2-chloro end products with 98% hydrazine hydrate according to standard procedures, e.g. where for X=NH, see Bednyagina, N. P. and Postovskii, I. Ya., *Zh Obshch Khim* 30, 1431, 1960; *Chem Abstr* 55:1586, (1961), for X=N—$CH_3$, see Kulkarni M. V. and Patil, V. D., *Arch Pharm* 314, 440, (1981), for X=O, see Katz, L, *J Am Chem Soc* 75, 712, (1953), and for X=S, see Katz, L, *J Am Chem Soc* 73, 4009, (1951).

The ketones of type III were synthesised by reacting the respective 2-cyano compounds with an appropriate Grignard reagent (RMgX), alkyl lithium or phenyl lithium reagent in analogy to known methods or to the patent literature (see Lutz, H. et al. DE 43 06 006-A)

Pharmacological Tests:

The surprising anti-tumor activities of the novel hydrazones and of the hydrazones already generally disclosed in the prior art of the present invention, respectively, are described in the following. As control, hydroxyurea, a commercially available chemotherapeutic anti-cancer agent is used.

Inhibition of Tumor Cell Growth.

In order to obtain information about the growth-inhibiting action on tumor cells, the inhibition of the growth of the following human tumor cells was determined: Burkitt's lymphoma (CA 46, ATCC No. CRL 1648), CCRF-CEM (acute lymphoblastic leukemia, ATCC No. CCL 119), K562 (chronic myelogenous leukemia, ATTC No. CCL 243), HeLa (epitheloid cervix carcinoma, ATCC No. CCL 2), MEXF 276L (melanoma), HT-29 (colon adenocarcinoma, ATCC No. HTB 38), KB-3-1 (human oral epidermoid carcinoma, CTCC No. CCL 17), KB-HU hydroxyurea-resistant, multidrug-resistant KB-C1 cells (Akiyama et al, *Cell. Mol Genet.*, 11:117–126, 1985). Burkitt's, CCRF-CEM, HeLa and MEXF 276L cells were grown in RPMI 1640, HT-29 cells in McCoy's 5A medium. The KB cell lines were grown in Dulbecco's modified Eagle's medium (4,5 g glucose/l). To the cultures of KB-C1 cells 1 µg of colchicine/ml, and to the hydroxyurea-resistant KB-HU cells 1 mM hydroxyurea was added every other week. The media were supplemented with 10% fetal calf serum (except Burkitt's lymphoma cells with 15%), 2 mM glutamine, 50 units/ml penicillin and 50 µg/ml streptomycin. Inhibition of growth of HeLa, HT-29, KB and MEXF 276L cells was detected by the SRB-assay (Skehan et al, J. Natl Cancer Inst., 82:1107–1112, 1990). 3,000 - 10,000 cells in 200 µl medium were seeded per well into 96-well plates. Dose-response curves for CCRF-CEM and Burkitt's lymphoma cells were effected by an MTT-assay (Mosman, J. Immunol Methods, 65:55–63, 1983) from Boehringer Mannheim, Mannheim, Germany. Approximately 10,000 cells per 100 µl were seeded in 96-well plates. After an initial incubation of four hours, various substance concentrations were added, and the cells were incubated at 37° C. in a water-saturated atmosphere of 95% air and 5% $CO_2$ for 72 hours. The substances were dissolved in dimethylsulfoxide (DMSO). The concentration of DMSO was 0.5%, and this was not toxic to the cells. Subsequently, the samples were fixed, washed, and the absorption was determined by a microplate reader. The results are shown in Tables 1–4.

TABLE 1

In vitro activity of compounds Ia against human tumor cell lines

Ia

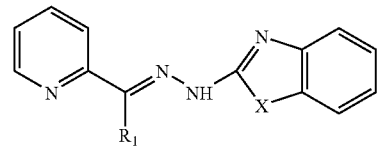

$IC_{50}$ (µM)

| Substance | $R_1$ | X | Burkitts | K562 | HeLa | HT-29 | KB-3-1 | KB-HU | KB-C1 |
|---|---|---|---|---|---|---|---|---|---|
| Ia-1 | H | NH | 0.66 | nt | 1.02 | 3.69 | 1.36 | nt | 2.94 |
| Ia-2 | | N—$CH_3$ | 0.03 | nt | 0.08 | 0.27 | nt | nt | nt |
| Ia-3 | | O | 0.005 | nt | 0.025 | 1.44 | 0.48 | 0.61 | 0.77 |
| Ia-4 | $CH_3$ | NH | 0.044 | nt | 0.07 | 0.49 | 0.51 | 0.90 | 1.97 |
| Ia-5 | | N—$CH_3$ | 0.0043 | nt | 0.0054 | 0.05 | 0.044 | 0.052 | 0.048 |
| Ia-6 | | O | 0.009 | nt | 0.023 | 0.13 | 0.21 | 0.32 | 0.61 |
| Ia-7 | $CH_2CH_3$ | NH | nt | nt | 0.053 | 0.24 | 4.01 | nt | 0.74 |
| Ia-8 | | N—$CH_3$ | 1.01 | 0.09 | 0.02 | 10.95 | nt | nt | nt |
| Ia-9 | | O | nt | nt | nt | nt | nt | nt | nt |
| Ia-10 | | S | nt | nt | nt | nt | nt | nt | nt |
| Ia-11 | $CH_2CH_2CH_3$ | NH | nt | nt | 0.057 | 0.20 | 0.50 | 0.13 | 0.83 |
| Ia-12 | | N—$CH_3$ | 1.78 | 0.08 | 0.017 | 16.30 | nt | nt | nt |
| Ia-13 | | O | nt | nt | nt | nt | nt | nt | nt |
| Ia-14 | | S | nt | nt | nt | nt | nt | nt | nt |
| Ia-15 | $CH(CH_3)_2$ | NH | nt | nt | 0.021 | 0.52 | 0.70 | 0.001 | 1.98 |
| Ia-16 | | N—$CH_3$ | nt | 0.05 | 0.006 | 5.58 | nt | nt | nt |
| Ia-17 | | O | nt | nt | nt | nt | nt | nt | nt |
| Ia-18 | | S | nt | nt | nt | nt | nt | nt | nt |
| Ia-19 | $C(CH_3)_3$ | NH | nt | nt | >100 | >100 | nt | nt | 92 |
| Ia-20 | | N—$CH_3$ | 8.43 | 1.68 | 0.53 | >100 | nt | nt | nt |
| Ia-21 | $C(CH_3)_3$ | O | nt | nt | nt | nt | nt | nt | nt |
| Ia-22 | $C(CH_3)_3$ | S | nt | nt | nt | nt | nt | nt | nt |
| Ia-23 | cyclopropyl | NH | nt | nt | 0.07 | 0.51 | nt | nt | 0.32 |
| Ia-24 | | N—$CH_3$ | nt | 0.04 | 0.002 | 2.88 | nt | nt | nt |
| Ia-25 | | O | nt | nt | nt | nt | nt | nt | nt |
| Ia-26 | | S | nt | nt | nt | nt | nt | nt | nt |
| Ia-27 | cyclohexyl | S | nt | nt | nt | nt | nt | nt | nt |
| Ia-28 | phenyl | NH | nt | nt | nt | nt | nt | nt | nt |
| Ia-29 | | N—$CH_3$ | nt | 0.06 | 0.009 | 8.74 | nt | nt | nt |
| Ia-30 | | O | nt | nt | nt | nt | nt | nt | nt |
| Ia-31 | | S | nt | nt | nt | nt | nt | nt | nt |
| Ia-32 | benzyl | NH | nt | nt | nt | nt | nt | nt | nt |
| Ia-33 | | N—$CH_3$ | nt | 0.12 | 0.024 | 14.10 | nt | nt | nt |

TABLE 1-continued

| | | | | | | | | |
|---|---|---|---|---|---|---|---|---|
| Ia-34 | | O | nt | nt | nt | nt | nt | nt |
| Ia-35 | | S | nt | nt | nt | nt | nt | nt |
| Ia-36 | 2-pyridyl | NH | nt | nt | 1.43 | 1.36 | nt | 2.11 |
| Ia-37 | | N—CH$_3$ | nt | 0.03 | 0.09 | 4.64 | nt | nt |
| Ia-38 | | O | nt | nt | nt | nt | nt | nt |
| Ia-39 | | S | nt | nt | nt | nt | nt | nt | nt = not tested

TABLE 2

In vitro-activity of compounds Ib against human tumor cell lines

Ib

Het—C(CH$_3$)=N—NH—[benzazole with X]

IC$_{50}$ (μM)

| Substance | Het. | X | MEXF276L | Burkitts | CCRF-CEM | HeLa | HT-29 |
|---|---|---|---|---|---|---|---|
| Ib-1 | pyridazinyl | NH | 2.14 | 0.84 | 0.98 | 1.23 | 2.06 |
| Ib-2 | pyridazinyl | N—CH$_3$ | nt | nt | nt | nt | nt |
| Ib-3 | pyridazinyl | O | 1.96 | 1.34 | 0.72 | 1.25 | 1.77 |
| Ib-4 | 6-methylpyridazin-3-yl | NH | 2.36 | 1.87 | 1.30 | 1.99 | 1.96 |
| Ib-5 | 6-methylpyridazin-3-yl | O | 2.25 | 0.84 | 0.46 | 1.61 | 1.04 |
| Ib-6 | pyrimidinyl | NH | 0.91 | 0.56 | 0.41 | 0.88 | 0.57 |
| Ib-7 | pyrimidinyl | N—CH$_3$ | nt | nt | nt | nt | nt |
| Ib-8 | pyrimidinyl | O | 1.30 | 0.14 | 0.34 | 0.41 | 0.23 |
| Ib-9 | 4,6-dimethylpyrimidinyl | NH | 1.14 | 0.39 | 0.66 | 0.89 | 0.36 |
| Ib-10 | 4,6-dimethylpyrimidinyl | O | 1.22 | 0.04 | 0.22 | 0.21 | 0.12 |
| Ib-11 | pyrazinyl | NH | 2.13 | 1.32 | 0.90 | 1.71 | 0.71 |
| Ib-12 | pyrazinyl | N—CH$_3$ | nt | nt | nt | nt | nt |
| Ib-13 | pyrazinyl | O | 1.09 | 0.31 | 0.52 | 0.56 | 0.48 |
| Ib-14 | 2,3-dimethylpyrazinyl | NH | 4.24 | 3.37 | 2.17 | 3.53 | 2.23 |
| Ib-15 | 2,3-dimethylpyrazinyl | O | 5.38 | 0.91 | 1.30 | 1.87 | 2.15 |
| Ib-16 | 2,5-dimethylpyrazinyl | NH | 2.00 | 1.22 | 0.84 | 1.49 | 0.88 |
| Ib-17 | 2,5-dimethylpyrazinyl | O | 1.66 | 0.15 | 0.62 | 0.37 | 0.28 |

TABLE 2-continued

| | | | | | | | |
|---|---|---|---|---|---|---|---|
| Ib-18 | 2-methylquinoline | NH | nt | nt | nt | nt | nt |
| Ib-19 | | O | >10 | 5.49 | 7.04 | 4.53 | 7.76 |
| Ib-20 | 1-methylisoquinoline | NH | nt | nt | nt | nt | nt |
| Ib-21 | | O | 1.56 | 0.20 | 0.35 | 0.34 | 1.93 |
| Ib-22 | 3-methylisoquinoline | NH | nt | nt | nt | nt | nt |
| Ib-23 | | N—CH$_3$ | nt | nt | nt | nt | nt |
| Ib-24 | | O | 0.65 | 0.025 | 0.13 | 0.063 | 0.23 |
| Ib-25 | 2-methylpyrimidine | NH | 0.96 | 0.22 | 0.20 | 0.63 | 0.42 |
| Ib-26 | | N—CH$_3$ | nt | nt | nt | nt | nt |
| Ib-27 | 2-methylpyrimidine | O | 0.70 | 0.03 | 0.13 | 0.18 | 0.27 | nt = not tested

TABLE 3

In vitro-activity of compounds Ic against human tumor cell lines

Ic

IC$_{50}$ (μM)

| Substance | R$_2$ | Burkitts | K562 | HeLa | HT-29 | KB-3-1 | KB-HU | KB-C1 |
|---|---|---|---|---|---|---|---|---|
| Ic-1 | CH$_2$CH$_3$ | 0.68 | 0.06 | 0.19 | 11.90 | | | |
| Ic-2 | CH$_2$CH$_2$CH$_3$ | 1.28 | 0.12 | 0.21 | 35.10 | | | |
| Ic-3 | CH(CH$_3$)$_2$ | 2.14 | 0.33 | 0.06 | 16.10 | | | |
| Ic-4 | C(CH$_3$)$_3$ | nt | nt | nt | nt | | | |
| Ic-5 | CH$_2$—CH=CH$_2$ | 0.98 | 0.18 | 0.01 | 12.80 | | | |
| Ic-6 | cyclopropyl | Nt | 0.09 | 0.40 | 11.20 | | | |
| Ic-7 | phenyl | 3.48 | 0.70 | 0.05 | 0.10 | | | |
| Ic-8 | benzyl | 3.58 | 0.45 | 0.13 | 0.16 | | | | nt = not tested

TABLE 4

In vitro-activity of compounds Id against human tumor cell lines

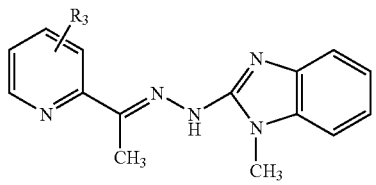

| Substance | R₃ | Burkitts | K562 | HeLa | HT-29 | KB-3-1 | KB-HU | KB-C1 |
|---|---|---|---|---|---|---|---|---|
| Id-1 | 3-OCH₃ | 0.001 | nt | 0.05 | 0.23 | 0.02 | 0.01 | 0.87 |
| Id-2 | 4-OCH₃ | 0.001 | nt | 0.05 | 0.12 | 0.05 | 0.04 | 0.16 |
| Id-3 | 3-Cl | 0.004 | nt | 0.25 | 0.54 | 0.31 | 0.18 | 0.30 |
| Id-4 | 4-Cl | 0.004 | nt | 0.17 | 0.52 | 0.071 | 0.27 | 0.09 |
| Id-5 | 6-Cl | 0.012 | nt | 0.19 | 0.32 | 0.007 | 0.02 | 0.03 |
| Id-6 | 6-Br | 2.49 | nt | 3.25 | 3.15 | 1.69 | 3.89 | 2.13 |
| Id-7 | 3-CH₃ | nt | nt | nt | nt | 0.26 | 0.46 | 0.16 |
| Id-8 | 4-CH₃ | nt | nt | nt | nt | 0.03 | 0.02 | 0.10 |
| Id-9 | 5-CH₃ | nt | nt | nt | nt | 0.04 | 0.12 | 0.11 |
| Id-10 | 6-CH₃ | 0.11 | nt | 0.38 | 0.80 | 0.49 | 2.23 | 1.80 |
| Id-11 | 3-N(CH₃)₂ | 0.002 | nt | 0.02 | 0.16 | 0.008 | 0.24 | 0.06 |
| Id-12 | 4-N(CH₃)₂ | 2.21 | nt | 3.74 | 5.07 | 2.28 | 0.05 | 0.81 |
| Id-13 | 6-N(CH₃)₂ | 2.01 | nt | 6.60 | 17.56 | 4.02 | 4.90 | 29.49 |
| Id-14 | 3-phenyl | 0.01 | nt | 0.07 | 0.07 | 0.55 | 0.70 | 1.42 |
| Id-15 | 4-phenyl | 0.03 | nt | 0.04 | 0.05 | 0.14 | 0.12 | 0.23 |
| Id-16 | 5-phenyl | 0.03 | nt | 0.18 | 0.25 | 0.25 | 0.19 | 0.18 |
| Id-17 | 6-phenyl | 1.45 | nt | 2.35 | 3.36 | 3.85 | 9.94 | 3.08 | nt = not tested

Colony Forming Assay as a More Precise In Vitro Study

In order to obtain more detailed information which types of tumor the compounds inhibit most efficiently, the colony formation of human tumor grafts was tested. An excellent correlation of drug response in patients and the colony forming assay has been found (Scholz et al, *Eur. J. Cancer* 25:901–905, 1990). Solid human tumors were grown as grafts in nude mice, removed from the latter, mechanically comminuted and subsequently incubated in an enzyme cocktail consisting of collagenase (1.2–1.8 U/ml), DNAse (375 U/ml) and hyaluronidase (29 U/ml) in RPMI 1640 medium at 37° C. for 30 minutes. The cell mixture was passed through sieves of 200 µm and 50 µm mesh size and washed thereafter twice with PBS (phosphate buffered saline). The percentage of live cells was determined using a Neubauer counting chamber and trypan blue staining.

The colony forming assay was performed according to a two-layer agar technique introduced and modified by Hamburger and Salmon (*Hamburger and Salmon, Science,* 197: 461–463, 1977). The bottom layer consisted of 0.2 ml of Iscoves's Modified Dulbecco's medium with 20% fetal calf serum and 0.75% agar. $8 \times 10^3$ to $1.6 \times 10^4$ cells were added to the same medium and 0.4% agar and plated in 24-multiwell plates onto the base layer. One day after the plating (with continuous exposure), the substances were added in 0.2 ml medium. Each plate included six controls containing the solvent only, and the treated groups contained 6 concentrations of the substances, each in triplicate. Cultures were incubated at 37° C. and 7% $CO_2$ in a water-saturated atmosphere for 3 to 6 days, depending on the doubling time of the tumor cells. At the time of maximum colony formation with a size of 50 µM, counts were performed with an automatic image analysis system. 24 h prior to counting, live colonies were stained with a sterile aqueous solution of 2-(4-iodophenyl)-3-(4-nitrophenyl)-5-phenyltetrazolium chloride (1 mg/ml, 100 µl/well). The results of the tests are given in FIG. 1, and in the following Table 5, respectively. In FIG. 1, columns pointing towards the left show that the respective cell lines are more sensitive than average. Columns pointing towards the right show a slighter than average activity. The following cell lines were assayed:

| Tumor | Cell line | Histology | Time of contact with test compound (days) |
|---|---|---|---|
| bladder | T24 | | |
| breast | MAXF 401NL | adenocarcinoma ER−, Pr− | 6 |
| | MCF-7 | adenocarcinoma ER+, Pr+ | 4 |
| | MDA-MB 468 | | |
| colon | HT-29 | moderately diff. adenocarcinoma | 3 |
| | SW620 | slightly diff. adenocarcinoma | 3 |
| colon | CXF 94L | | |
| stomach | GXF 251L | adenocarcinoma | 4 |
| lungs - small cell | DMS 114 | | |
| | DMS 273 | | |
| lungs - non small cell | LXFA 526L | adenocarcinoma | |
| | LXFA 629L | adenocarcinoma | 4 |
| | LXFE 66L | epidermoid carcinoma | 4 |
| | LXFL 529L | large cell carcinoma | |
| | LXFL 1072L | large cell carcinoma | |
| melanoma | MEXF 462NL | amelanoidal melanoma | 4 |
| | MEXF 514NL | melanoidal melanoma | 4 |
| ovarian | OVCAR3 | adenocarcinoma | 6 |
| | OVXF 899L | | |
| prostate | DU145 | | |
| | PC3M | | |
| renal | RXF 486L | hypernephroma | 4 |
| | RXF 944L | hypernephroma | 4 |
| uterus | UXF 1138L | carcinosarcoma | 4 |

ER = estrogen receptor,
Pr = progesterone receptor,
(−) = negative,
(+) = positive

TABLE 5

(mean values of all cell lines tested in FIG. 1)

| Substance | Mean IC$_{50}$ (μM) | Mean IC$_{70}$ (μM) | Mean IC$_{90}$ (μM) |
| --- | --- | --- | --- |
| Ia-12 | 0.246 | 0.603 | 3.736 |
| Ia-16 | 0.188 | 0.521 | 3.769 |
| Ia-20 | 0.015 | 0.064 | 0.231 |
| Ia-24 | 0.138 | 0.387 | 3.135 |
| Ia-29 | 0.294 | 0.741 | 4.664 |
| Ic-3 | 0.265 | 0.750 | 4.301 |
| Ic-5 | 0.214 | 0,607 | 3.334 |
| Ic-7 | 0.760 | 1.741 | 6.296 |
| Id-2 | 0.080 | 0.261 | 2.851 |
| Id-4 | 0.301 | 0.956 | 4.294 |
| Id-5 | 3.303 | 5.740 | 9.381 |
| Id-8 | 0.102 | 0.317 | 2.385 |
| Id-9 | 0.199 | 0.560 | 3.793 |
| Id-11 | 0.137 | 0.397 | 2.895 |
| Id-15 | 0.429 | 1.017 | 5.666 |
| Id-16 | 0.965 | 2.084 | 7.449 |

As shown in Table 5, compounds of the present invention exhibit excellent in vitro anti-tumor activities (IC$_{50}$) against human cancer cells. In comparison, the activity of hydroxyurea is far lower than that of the compounds according to the invention (cf. FIG. 1). The IC$_{70}$ pattern of the substances is very similar, from which it can be concluded that they have an identical mode of action. Furthermore, compounds Id-2, Id-8, Ia-24, Ia-16, Ia-9, Ic-5, Ia-29, and Id-4 showed selectivity for colon, breast, ovarian, and uterus tumors.

Substances Ib-11 and Ib-24 were also tested in the so-called hollow fibre assay for their anti-tumor activity. For this purpose, mice were implanted with up to 12 different tumor cells in permeable hoses and treated with the compounds according to the invention. In these tests it was confirmed that substances Ib-11 and Ib-24 exhibit anti-tumor activity.

Furthermore, some presently used anti-tumor compounds have already been shown to be capable of inducing apoptosis (programmed cell death) of tumor cells. Surprisingly, also some of the compounds of the invention are capable of inducing apoptosis, e.g. compounds Id-12 and Id-17.

In non-treated Burkitt's lymphoma cells, an average of 1.7% are apoptotic. If these cells are treated with twice the IC$_{50}$ concentrations of compound Id-12 for 48 hours, 60% of the cells are apoptotic, when using the compound Id-17, it is 85%. Treatment with hydroxyurea as control resulted in 7.3% of apoptosis. The determination of the apoptosis was performed with propium iodide (Nicoletti et al., *Rapid and Simple Method for Measuring Thymocyte Apoptosis by Propium Iodine Staining and Flow Cytometry, J. Immunol. Methods,* 139, 271–279, 1991).

Human Tumor Xenografts in Nude Mice

Human CXF 280 tumor cells were implanted subcutaneously into the flanks of six to eight week old female athymic nude mice of the Balb/C strain which are homozygous for the nude gene. When tumors were approximately 5–7 mm in diameter, mice were randomly assigned to the control group or to the group to be treated. The control group consisted of 4 mice which had 6 evaluable tumors. The group to be treated consisted of 3–4 mice which had 4–5 evaluable tumors. Substance Ia-5 was applied i.p. as a fine suspension at doses of 60, 30 and 10 mg/kg/day on days 0, 4 and 8. Mice were weighed twice a week, and the tumor volumes were measured using callipers. The tumor volume was calculated according to the following formula: tumor volume (mm$^3$) =width (mm$^2$)×length (mm)/2. Relative tumor volume (RTV) values were calculated for each single tumor by dividing the tumor volume on day X (TV$_x$) by the tumor volume on day 0 (TV$_0$) at the time of randomisation [RTV= (TV$_x$×100)/TV$_0$)]. The mean RTV values were used for further evaluation.

Figure 1:
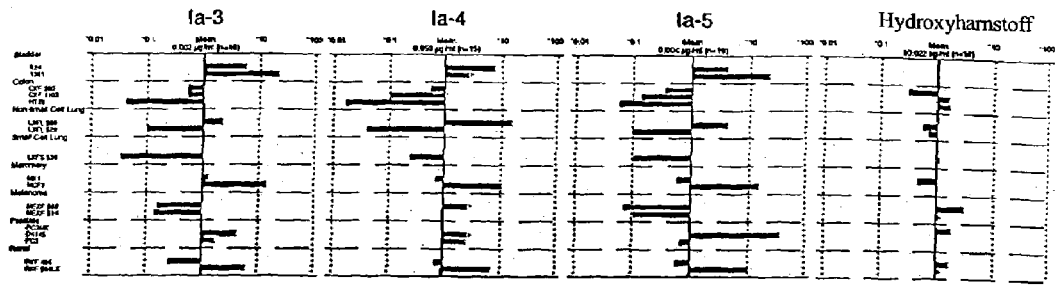
Figure 2:
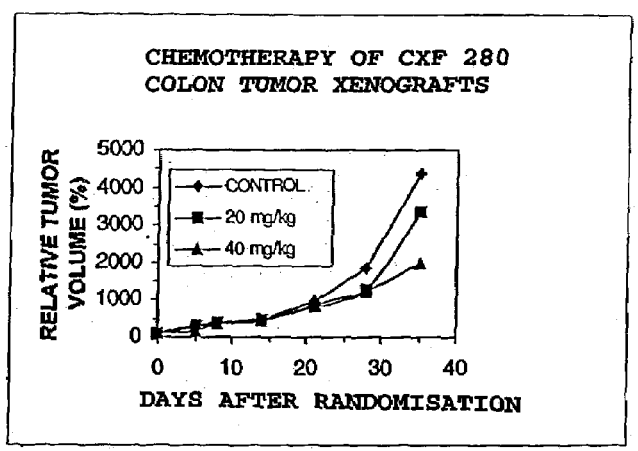
FIG. 2 shows the change of tumor volume after substance Ia-5 of the present invention was administered to mice into which human tumors had been transplanted.
Figure 3:
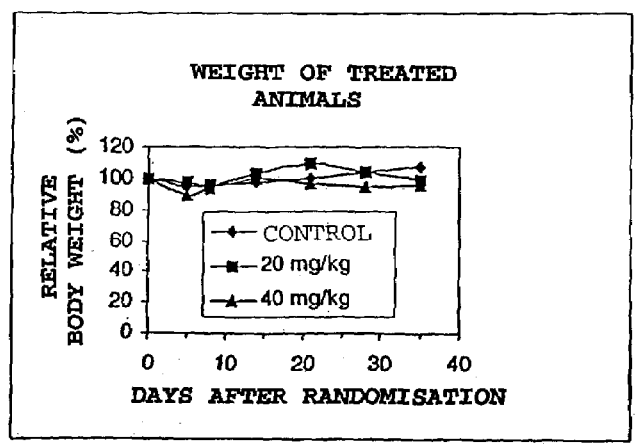
FIG. 3 shows the change of body weight over time if the substance Ia-5 of this invention was administered to mice into which human CXF 280 colon tumors had been transplanted (reduction of weight during treatment is a measure for the toxicity of the substance).

The production of compounds of the present invention will now be explained by way of the following examples to which, however, it shall not be restricted. The NMR data indicated relate to measurement in DMSO-d6.

EXAMPLE 1

1-(2-Pyridyl)-1-ethanon-1(1H-benzo[d]imidazol-2-yl)-hydrazone (1a-4)

A mixture of 2-acetyl pyridine (1.00 g, 8.25 mmol) and 2-hydrazinobenzimidazole (1.22 g, 8.25 mmol) in 20 ml of methanol is stirred for 3 days at room temperature after addition of 6 drops of glacial acetic acid. The reaction is monitored by means of thin layer chromatography (Polygram Sil G/UV$_{254}$ prefabricated foils; eluting agent: CH$_2$Cl$_2$:MeOH (12:1)). Subsequently, the reaction mixture is diluted with distilled water until a precipitate forms and stored in the refrigerator at approximately 5° C. for 24 hours. The precipitate is filtered, washed several times with 50% methanol, and dried. The product is recrystallized from a mixture of ethyl acetate and diisopropyl ether. Yield: 1.45 g (70% of theory).

C14H$_{13}$N$_5$ (251.29)

| CHN: | Calculated | C 66.92% | H 5.21% | N 27.87% |
| --- | --- | --- | --- | --- |
| | Found | C 66.79% | H 5.47% | N 27.64% |

$^1$H-NMR (δ, ppm)=2.39 (s, 3H, CH$_3$), 6.94–7.04 (m, 2H, arom. H), 7.20–7.36 (m, 3H, arom. H), 7.82 (ddd, 1H, pyridine-H4, J=8.1, 7.4, 1.9 Hz), 8.48 (br d, 1H, arom. H), 8.56 (ddd, 1H, pyridine-H6, J=4.9, 1.8, 0.8 Hz), 10.85 (br s, 1H, NH), 11.51 (br s, 1H, NH).

EXAMPLE 2

1-(2-Pyridyl)-1-propanone-1-(1,3-benzoxazol-2-yl)-hydrazone (1a-13)

A mixture of 2-propionyl pyridine (0.60 g, 4.42 mmol) and 2-hydrazinobenzoxazole (0.60 g 4.02 mmol) in 25 ml of methanol is refluxed for 24 hours after the addition of 6 drops of glacial acetic acid. The reaction mixture is stored over night in the refrigerator at approximately 5° C. The precipitate is filtered and recrystallized from diisopropyl ether. Yield: 0.68 g (64% of theory).

$C_{15}H_{14}N_4O$ (266.31)

| CHN: | Calculated | C 67.65% | H 5.30% | N 21.04% |
|---|---|---|---|---|
| | Found | C 67.76% | H 5.28% | N 21.24% |

$^1$H-NMR (δ, ppm) 1.08 (t, 3H), 3.05 (q, 2H), 7.05–7.46 (m, 4H), 7.37 (qd, 1H), 7.84 (ddd, 1H), 8.22 (br.s 1H), 8.60 (qd, 1H), 11.48 (br.s, 1H).

EXAMPLE 3

E/Z-Cyclopropyl-(2-pyridyl)-methanone-(1-methyl-1H-benzo[d]imidazol-2-yl)-hydrazone (1a-24)

A mixture of cyclopropyl-(2-pyridyl)-methanone (1,00 g, 7,40 mmol) and 1-methyl-2-hydrazinobenzimidazole (1.20 g, 7.40 mmol) in 20 ml of methanol is stirred for 3 days at room temperature after the addition of 6 drops of glacial acetic acid. Monitoring is effected by means of thin layer chromatography (Polygram Sil G/UV$_{254}$ prefabricated foils; eluting agent: CH$_2$Cl$_2$:MeOH (12:1)). Subsequently, the reaction mixture is diluted with distilled water until a precipitate forms and stored in the refrigerator at approximately 5° C. for 24 hours. The precipitate is filtered, washed several times with 50% methanol, and dried. The product is recrystallized from a mixture of methanol and water. Yield: 0.97 g (45% of theory).

$C_{17}H_{17}N_5$ (291.36)

| CHN: | Calculated | C 70.07% | H 5.88% | N 24.05% |
|---|---|---|---|---|
| | Found | C 70.37% | H 6.08% | N 24.04% |

$^1$H-NMR (δ ppm)=0.71–1.04 (m, 4H, cyclopropyl-CH$_2$—CH$_2$), 2.08–2.35 (m, 1H, cyclopropyl-CH), 2.95–3.05 (m, 1H, cyclopropyl-CH), 3.25 (s, 1H, N—CH$_3$), 3.42 (s, 1H, N—CH$_3$), 3.81 (s, 1H, N—CH$_3$), 6.91–7.17 (m, pyridine-H+arom. H), 7.21–7.40 (m, pyridine-H+arom. H), 7.54–7.62 (m, pyridine-H+arom. H) 7.70–7.84 (m, pyridine-H+arom. H), 8.11–8.28 (m, pyridine-H+arom. H), 8.45 (br. d, 1H, pyridine-H6), 8.64 (br. d, 1H, pyridine-H6), 8.85 (br. d, 1H, pyridine-H6), 10.64 (br. s, 1H, NH), 10.88 (br. s, 1H, NH), 14.61 (br. s, 1H, NH).

EXAMPLE 4

Cyclohexyl-(2-pyridyl)-methanone-(1,3-benzothiazol-2-yl)-hydrazone (1a-27)

A mixture of cyclohexyl-(2-pyridyl)-methanone (0.77 g, 4.05 mmol) and 2-hydrazinobenzothiazole (0.60 g, 4.02 mmol) in 15 ml of methanol is refluxed for 15 hours after the addition of 5 drops of glacial acetic acid. The reaction is monitored by means of thin layer chromatography (Polygram Sil G/UV$_{254}$ prefabricated foils; eluting agent: petroleum ether:ethyl acetate (3:7)). The reaction mixture is stored over night in the refrigerator at approximately 5° C. The precipitate is filtered and recrystallized from a mixture of ethanol and water. Yield: 1.09 g (80% of theory).

$C_{19}H_{20}N_4S$ (336.46)

| CHN: | Calculated | C 67.83% | H 5.99% | N 16.65% |
|---|---|---|---|---|
| | Found | C 67.79% | H 6.23% | N 16.24% |

$^1$H-NMR (δ, ppm)=1.15–1.59 (m, 5H), 1.63–2.04 (m, 5H), 2.86–3.09 (br.s, 1H), 7.07–8.06 (m, 7H), 8.80 (d, 1H), 14.43 (br.s, 1H).

EXAMPLE 5

1-(4-Pyrimidinyl)-1-ethanone-1-(1H-benzo[d]imidazol-2-yl)-hydrazone (1b-6)

A mixture of 4-acetyl pyrimidine (0.412 g, 3.37 mmol) and 2-hydrazinobenzimidazole (0.50 g, 3.37 mmol) in 15 ml of methanol is refluxed after the addition of 5 drops of glacial acetic acid, until monitoring of the reaction by means of thin layer chromatography (Polygram Sil G/UV$_{254}$ prefabricated foils; eluting agent: CH$_2$Cl$_2$:MeOH (10:1)) did not reveal any further reaction. The reaction mixture is stored over night in the refrigerator at approximately 5° C. The precipitate is filtered and recrystallized from a mixture of ethyl acetate and diisopropyl ether. Yield: 0.65 g (76% of theory).

$C_{13}H_{12}N_6$ (252.28)

| CHN: | Calculated | C 61.89% | H 4.79% | N 33.31% |
|---|---|---|---|---|
| | Found | C 61.79% | H 4.82% | N 33.24% |

$^1$H-NMR (δ, ppm)=2.36 (s, 3H), 7.01–7.07 (m, 2H), 7.20–7.27 (m, 2H), 8.50 (dd, 1H), 8.75 (d, 1H), 9.14 (d, 1H), 10.67 (br. s, 2H).

EXAMPLE 6

1-(2-Pyrazinyl)-1-ethanone-1-(1,3-benzoxazol-2-yl)-hydrazone (1b-13)

A mixture of 4-acetylpyrazine (0.41 g, 3.35 mmol) and 2-hydrazinobenzoxazole (0.50 g, 3.35 mmol) in 15 ml of methanol is refluxed after the addition of 5 drops of glacial acetic acid, until monitoring of the reaction by means of thin layer chromatography (Polygram Sil G/UV$_{254}$ prefabricated foils; eluting agent: petroleum ether:ethylacetate (3:7) does not reveal any further reaction (approximately 15 hours). The reaction mixture is stored over night in the refrigerator at approximately 5° C. The precipitate is filtered and recrystallized from methanol. Yield: 0.75 g (80% of theory).

$C_{13}H_{11}N_5O$ (253.27)

| CHN: | Calculated | C 61.65% | H 4.38% | N 27.65% |
|---|---|---|---|---|
| | Found | C 61.82% | H 4.52% | N 28.04% |

$^1$H-NMR (δ, ppm)=2.38 (s, 3H), 7.04–7.46 (m, 4H), 8.58 (dd, 1H), 8.60 (dd, 1H), 9.47 (br. s, 1H), 11.63 (br. s, 1H).

EXAMPLE 7

1-(3-Isoquinolinyl)-1-ethanone-1-(1-methyl-1H-benzo[d]imidazol-2-yl)-hydrazone (1b-23)

A mixture of 3-acetylisoquinoline (1.01 g, 5.9 mmol) and 1-methyl-2-hydrazinobenzimidazole (0.96 g, 5.55 mmol) in 15 ml of methanol is stirred for approximately 7 days at room temperature after the addition of 5 drops of glacial acetic acid. The reaction is monitored by means of thin layer chromatography (Polygram Sil G/UV$_{254}$ prefabricated foils; eluting agent: petroleum ether:ethyl acetate (3:7)). The reaction mixture is stored over night in the freezer at approximately −20° C. The precipitate is filtered, washed with ether and dried. The product is recrystallized from a mixture of ethylacetate and petroleum ether. Yield: 1.66 g (95% of theory).

$C_{19}H_{17}N_5$ (315.38)

| CHN: | Calculated | C 72.36% | H 5.43% | N 22.21% |
|---|---|---|---|---|
| | Found | C 72.28% | H 5.31% | N 22.45% |

$^1$H-NMR (δ, ppm)=2.54 (s, 3H), 3.32 (s, 3H), 3.48 (s, 3H), 6.99–7.06 (m, 2H), 7.11–7.18 (m, 2H), 7.62 (ddd, 1H), 7.77 (ddd, 1H), 7.97 (d, 1H), 8.10 (d, 1H), 8.79 (s, 1H), 9.31 (s, 1H), 11.06 (s, 1H).

EXAMPLE 8

1-(2-Pyridyl)-1-ethanone-1-(1-ethyl-1H-benzo[d]imidazol-2-yl)hydrazone (1c-1)

A mixture of 2-acetyl pyridine (0.62 g, 5.11 mmol) and 1-ethyl-2-hydrazinobenzimidazole (0.90 g, 5.11 mmol) in 20 ml of methanol is stirred at room temperature for 24 hours after the addition of 6 drops of glacial acetic acid. The reaction is monitored by means of thin layer chromatography (Polygram Sil G/UV$_{254}$ prefabricated foils; eluting agent: CH$_2$Cl$_2$:MeOH (12:1)). Subsequently, the reaction mixture is diluted with distilled water until a precipitate forms and stored for 24 hours in the refrigerator at approximately 5° C. The precipitate is filtered, washed several times with 50% methanol and dried. The product is recrystallized from a mixture of methanol and water. Yield: 0.99 g (70% of theory).

$C_{16}H_{17}N_5$ (279.35)

| CHN: | Calculated | C 68.80% | H 6.13% | N 25.07% |
|---|---|---|---|---|
| | Found | C 68.79% | H 6.23% | N 25.24% |

$^1$H-NMR (δ, ppm)=1.29 (t, 3H), 2.43 (s, 3H), 4.03 (q, 2H). 6.98–7.20 (m, 4H). 7.31 (ddd, 1H), 7.76 (ddd, 1H), 8.48 (d, 1H), 8.53 (ddd, 1H), 11.06 (br. s, 1H).

EXAMPLE 9

1-(2-Pyridyl)-1-ethanone-1-(1-phenyl-1H-benzo[d]imidazol-2-yl)-hydrazone (1c-7)

A mixture of 2-acetyl pyridine (1.00 g, 8.26 mmol) and 1-phenyl-2-hydrazinobenzimidazole (1.85 g, 8.26 mmol) in 20 ml of methanol is stirred at room temperature for 2 days after the addition of 6 drops of glacial acetic acid. The reaction is monitored by means of thin layer chromatography (Polygram Sil G/UV$_{254}$ prefabricated foils; eluting agent: CH$_2$Cl$_2$:MeOH (12:1)). Subsequently, the reaction mixture is diluted with distilled water until a precipitate forms and stored for 24 hours in the refrigerator at approximately 5° C. The precipitate is filtered, washed several times with 50% methanol, and dried. The product is recrystallized from a mixture of methanol and water. Yield: 1.35 g (50% of theory).

$C_{20}H_{17}N_5$ (327.39)

| CHN: | Calculated | C 73.37% | H 5.23% | N 21.39% |
|---|---|---|---|---|
| | Found | C 73.56% | H 5.39% | N 21.56% |

$^1$H-NMR (δ, ppm)=2.29 (s, 3H), 6.92–7.84 (m, 11H), 8.46–8.58 (m, 2H), 11.25 (br. s, 1H).

EXAMPLE 10

1-(3-Methoxy-2-pyridyl)-1-ethanone-1-(1-methyl-1H-benzo[d]imidazol-2-yl)-hydrazone (1d-1)

A mixture of 2-acetyl-3-methoxypyridine (0.50 g, 3.31 mmol) and 1-methyl-2-hydrazinobenzimidazole (0.54 g, 3.31 mmol) in 10 ml of methanol is stirred at room temperature for 3 days after the addition of 6 drops of glacial acetic acid. The reaction is monitored by means of thin layer chromatography (Polygram Sil G/UV$_{254}$ prefabricated foils; eluting agent: CH$_2$Cl$_2$:MeOH (12:1)). Subsequently, the reaction mixture is diluted with distilled water until a precipitate forms and stored for 24 hours in the refrigerator at approximately 5° C. The precipitate is filtered, washed several times with water, and dried. The product is recrystallized from a mixture of 20 ml of methanol and 10 ml of water. Yield: 0.87 g (89% of theory).

$C_{16}H_{17}N_5O$ (295.34)

| CHN: | Calculated | C 65.07% | H 5.80% | N 23.71% |
|---|---|---|---|---|
| | Found | C 63.60% | H 5.64% | N 23.21% |
| | x0.36 H$_2$O | C 63.67% | H 5.92% | N 23.20% |

$^1$H-NMR (δ, ppm)=2.29 (br. s, 3H, E-isomer), 2.57 (br. s, 3H, Z-isomer), 3.49 (br. s, 3H, Z-isomer), 4.42 (br. s, 3H, E-isomer), 3.81 (br. s, 3H), 6.84–7.10 (m, 4H), 7.31 (dd, 1H), 7.46 (dd, 1H), 8.16 (dd, 1H), 10.59 (br. s, 1H, E-isomer), 13.25 (br. s, 1H, Z-isomer).

EXAMPLE 11

1-(4-Chloro-2-pyridyl)-1-ethanone-1-(1-methyl-1H-benzo[d]imidazol-2-yl)-hydrazone (1d-4)

A mixture of 2-acetyl-4-chloropyridine (0.50 g, 3.20 mmol) and 1-methyl-2-hydrazinobenzimidazole (0.52 g, 3.20 mmol) in 5 ml of methanol is stirred for 4 days at room temperature after the addition of 6 drops of glacial acetic acid. The reaction is monitored by means of thin layer chromatography (Polygram Sil G/UV$_{254}$ prefabricated foils; eluting agent: CH$_2$Cl$_2$:MeOH (12:1)). Subsequently, the reaction mixture is diluted with distilled water until a precipitate forms and stored for 24 hours in the refrigerator at approximately 5° C. The precipitate is filtered, washed several times with water, and dried. The product is recrys tallized from a mixture of methanol and water. Yield: 0.60 g (62% of theory).

C₁₅H₁₄ClN₅ (327.39)

| CHN: | Calculated | C 60.10% | H 4.71% | N 23.36% |
|---|---|---|---|---|
| | Found | C 58.40% | H 4.55% | N 22.76% |
| | ×0.47 H₂O | C 58.45% | H 4.89% | N 22.72% |

¹H-NMR (δ, ppm)=2.40 (s, 3H), 3.49 (s, 3H), 6.99–7.22 (m, 4H), 7.37 (dd, 1H), 8.50 (d, 1H), 8.56 (d, 1H), 11.25 (br. s, 1H).

EXAMPLE 12

1-(5-Methyl-2-pyridyl)-1-ethanone-1-(1-methyl-1H-benzo[d]imidazol-2-yl)-hydrazone (1d-9)

A mixture of 2-acetyl-5-methylpyridine (1.00 g, 7.40 mmol) and 1-methyl-2-hydrazinobenzimidazole (1.20 g, 7.40 mmol) in 20 ml of methanol is stirred for 3 days at room temperature after the addition of 6 drops of glacial acetic acid. The reaction is monitored by means of thin layer chromatography (Polygram Sil G/UV₂₃₄ prefabricated foils; eluting agent: CH₂Cl₂:MeOH (12:1)). Subsequently, the reaction mixture is diluted with distilled water until a precipitate forms and stored for 24 hours in the refrigerator at approximately 5° C. The precipitate is filtered, washed several times with 50% methanol, and dried. The product is recrystallized from a mixture of methanol and water: Yield: 1.54 g (73% of theory).

C₁₆H₁₇N₅ (279.34)

| CHN: | Calculated | C 68.80% | H 6.13% | N 25.07% |
|---|---|---|---|---|
| | Found | C 68.58% | H 6.42% | N 24.97% |

¹H-NMR (δ, ppm) 2.23 (s, 3H), 2.40 (s, 3H), 3.46 (s, 3H), 6.93–7.14 (m, 4H), 7.59 (dd, 1H), 8.34–8.42 (m, 2H), 11.00 (br. s, 1H).

EXAMPLE 13

1-(6-Phenyl-2-pyridyl)-1-ethanone-1-(1-methyl-1H-benzo[d]imidazol-2-yl)-hydrazone (1d-17)

A mixture of 2-acetyl-6-phenylpyridine (0.50 g, 2.53 mmol) and 1-methyl-2-hydrazinobenzimidazole (0.41 g, 2.53 mmol) in 10 ml of methanol is stirred at room temperature for 12 hours after the addition of 6 drops of glacial acetic acid. The reaction is monitored by means of thin layer chromatography (Polygram Sil G/UV₂₅₄ prefabricated foils; eluting agent: CH₂Cl₂:MeOH (12:1)). Subsequently, the reaction mixture is diluted with distilled water until a precipitate forms and stored for 24 hours in a refrigerator at approximately 5° C. The precipitate is filtered, washed several times with water, and dried. The product is recrystallized from a mixture of methanol and water. Yield: 0.51 g (59% of theory).

C₂₁H₁₉N₅ (341.42)

| CHN: | Calculated | C 73.88% | H 5.61% | N 20.51% |
|---|---|---|---|---|
| | Found | C 70.24% | H 5.93% | N 19.44% |
| | ×0.92 H₂O | C 70.25% | H 5.91% | N 19.44% |

¹H-NMR (δ, ppm)=2.55 (s, 3H), 3.49 (br. s, 3H), 6.95–7.20 (m, 4H), 7.38–7.58 (m, 3H), 7.80–7.85 (m, 2H), 8.15–8.20 (m, 2H), 8.44–8.50 (m, 1H), 11.10 (br. s, 1H).

What is claimed is:

1. A compound of the general formula:

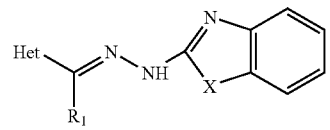

wherein Het=

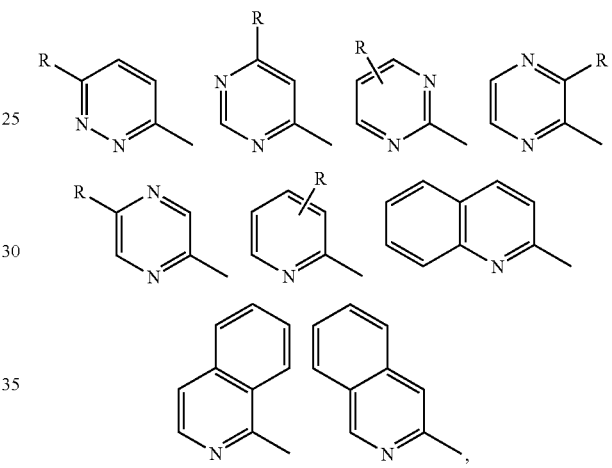

and wherein R=H, CH₃, OCH₃, OH, Cl, Br, F, CF₃, NO₂, NH₂, NHCOCH₃, N(CH₃)₂, phenyl, CN, C=NH(NH₂), C=S(NH₂), C=NH(NHOH), COOH or COOR₄, wherein R₄=an aliphatic residue or a phenyl group, or CONR₅R₆, wherein R₅ and R₆ are H, an aliphatic substituent or a phenyl group, R₁=H, methyl, ethyl, propyl, iso-propyl, butyl, tert-butyl, cyclopropyl, cyclohexyl, phenyl, benzyl or 2-pyridyl, and X=NH or N—R₂, wherein R₂=methyl, ethyl, propyl, sec.-propyl, butyl, tert.-butyl, allyl, cyclopropyl, phenyl, benzyl, CH₂—CH₂—O—CH₃ or CH₂—CH₂-n(CH₃)₂, with the proviso that if

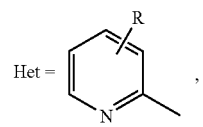

wherein R=H,
in case X=N: R₁ is not H,
in case X=NH: R₁ is not methyl,
in case X=N—R₂ with R₂=CH₃: R₁ is not methyl; as well as the pharmaceutically acceptable salts thereof.

2. A compound according to claim 1, namely

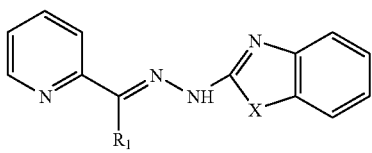

wherein R₁=H, methyl, ethyl, propyl, iso-propyl, butyl, tert.-butyl, cyclopropyl, cyclohexyl, phenyl, benzyl or 2-pyridyl, and X=NH, or NCH₃, with the proviso that if X=NH, R₁ is not methyl;

in case X=NCH₃: R₁ is not methyl; as well as the pharmaceutically acceptable salts thereof.

3. A compound according to claim 1, namely

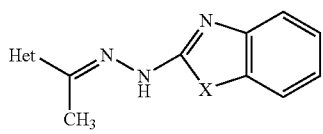

wherein Het=

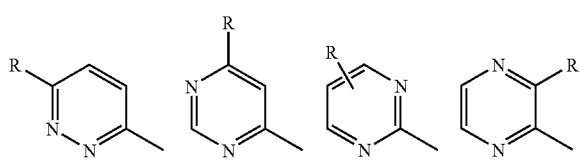

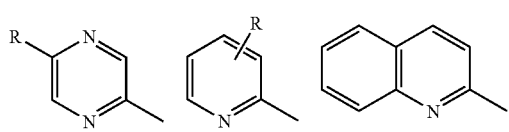

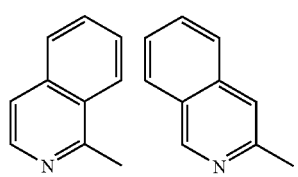

R=H or CH₃, X=NH, or N—CH₃, with the proviso that if

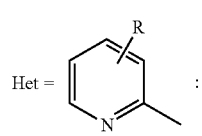

R is not H, as well as the pharmaceutically acceptable salts thereof.

4. A compound according to claim 1, namely

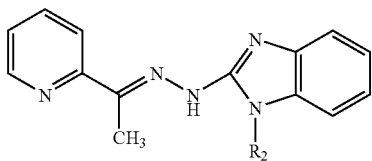

wherein R₂=ethyl, propyl, sec.-propyl, butyl, tert.-butyl, allyl, cyclopropyl, phenyl, benzyl or CH₂—CH₂—O—CH₃, CH₂—CH₂—N(CH₃)₂, as well as the pharmaceutically acceptable salts thereof.

5. A compound according to claim 1, namely

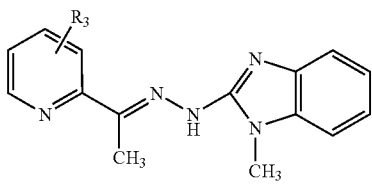

wherein R₃ is a 3, 4, 5 or 6-substituent and represents OCH₃, OH, Cl, Br, F, CH₃, CF₃, NO₂, NH₂, NHCOCH₃, N(CH₃)₂, phenyl, CN, C=NH(NH₂), C=S(NH₂), C=NH(NHOH), COOH or COOR₄, wherein R₄ is an aliphatic residue, a phenyl group or CONR₅R₆, wherein R₅ and R₆ are H, an aliphatic substituent or a phenyl group, as well as the pharmaceutically acceptable salts thereof.

6. A method of preparing a compound of the general formula

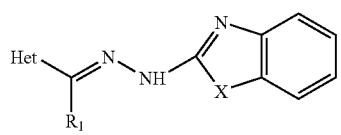

wherein Het=

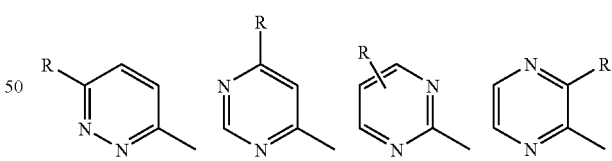

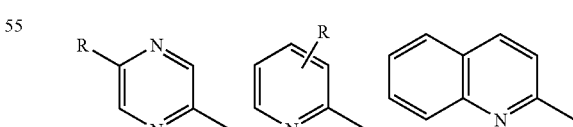

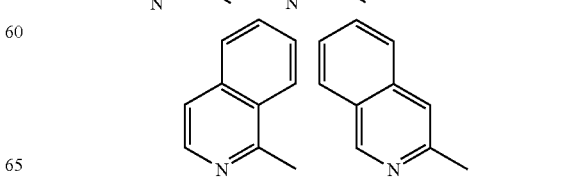

and wherein R=H, $CH_3$, $OCH_3$, OH, Cl, Br, F, $CF_3$, NO2, $NH_2$, $NHCOCH_3$, $N(CH_3)_2$, phenyl, CN, C=NH$(NH_2)$, C=S$(NH_2)$, C=NH(NHOH), COOH or $COOR_4$, wherein $R_4$ is an aliphatic residue or a phenyl group, or $CONR_5R_6$, wherein $R_5$ and $R_6$ are H, an aliphatic substituent or a phenyl group, $R_1$=H, methyl, ethyl, propyl, iso-propyl, butyl, tert.-butyl, cyclopropyl, cyclohexyl, phenyl, benzyl, or 2-pyridyl, and X=O, S, NH or N—$R_2$, wherein $R_2$=methyl, ethyl, propyl, sec-propyl, butyl, tert.-butyl, allyl, cyclopropyl, phenyl, benzyl, $CH_2$—$CH_2$—O—$CH_3$ or $CH_2$—$CH_2$—N$(CH_3)_2$, with the proviso that if X=S and Het=pyridinyl, then $R_1$ is not H or methyl, characterised in that a ketone of the general formula (III)

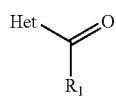

III wherein Het and $R_1$ are as defined above, is reacted with a hydrazine of the general formula (II)

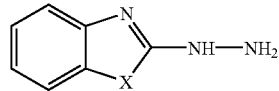

II wherein X is as defined above in the general formula.

7. A method according to claim 6, characterised in that the reaction is carried out in methanol or ethanol.

8. A method according to claim 6 or 7, characterised in that the reaction is carried out in the presence of a catalytic amount of an acid selected from the group consisting of acetic acid, hydrochloric acid or sulphuric acid.

* * * * *

UNITED STATES PATENT AND TRADEMARK OFFICE
CERTIFICATE OF CORRECTION

PATENT NO. : 7,112,680 B2  Page 1 of 1
APPLICATION NO. : 10/297306
DATED : September 26, 2006
INVENTOR(S) : Johann Hofmann et al.

It is certified that error appears in the above-identified patent and that said Letters Patent is hereby corrected as shown below:

Title Page item 73 should read -

\*\*Assignee: Austria Wirtschaftsservice
Gesellschaft mit beschrankter Haftung
Ungargasse 37, A - 1030 Wien, Vienna, (AT)

Assignee: Hofmann, Johann
Institut für Medizinische Chemie und
Biochemie der Universität
Innsbruck, Fritz-Pregl-Straße 3, A-6020
Innsbruck, (AT)

Assignee: Heinisch, Gottfried
Institut für Pharmazie
Innrain 52A, A-6020
Innsbruck, (AT)

Assignee: Easmon, Johnny
Institut für Pharmazie,
Innrain 52A, A-6020
Innsbruck, (AT)

Assignee: Pürstinger, Gerhard
Institut für Pharmazie,
Innrain 52A, A-6020
Innsbruck, (AT)

Assignee: Fiebig, Heinz-Herbert
Oncotest GmbH
Am Flughafen 12, D-79108
Freiburg, (DE)\*\*

Signed and Sealed this

Twenty-sixth Day of January, 2010

David J. Kappos
*Director of the United States Patent and Trademark Office*